US008688235B1

(12) United States Patent
Pianca et al.

(10) Patent No.: US 8,688,235 B1
(45) Date of Patent: Apr. 1, 2014

(54) LEAD WITH TRANSITION AND METHODS OF MANUFACTURE AND USE

(75) Inventors: Anne M. Pianca, Santa Monica, CA (US); Mathew J. Phillips, Sylmar, CA (US); Joshua D. Howard, Fresno, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1411 days.

(21) Appl. No.: 12/177,823

(22) Filed: Jul. 22, 2008

(51) Int. Cl.
*A61F 7/00* (2006.01)
(52) U.S. Cl.
USPC .......................................................... 607/122
(58) Field of Classification Search
USPC .................................. 607/115–117, 119, 122
See application file for complete search history.

(56) References Cited

U.S. PATENT DOCUMENTS

| | | | |
|---|---|---|---|
| 3,972,548 A | 8/1976 | Roseen | |
| 4,502,492 A * | 3/1985 | Bornzin | 607/121 |
| 4,592,372 A * | 6/1986 | Beranek | 607/119 |
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,723,113 B1 | 4/2004 | Shkolnik | |
| 6,741,892 B1 | 5/2004 | Meadows et al. | |
| 7,326,083 B2 * | 2/2008 | Mehdizadeh et al. | ... 439/607.12 |
| 7,395,116 B2 * | 7/2008 | Mehdizadeh et al. | .......... 607/37 |
| 2004/0059392 A1 | 3/2004 | Parramon et al. | |
| 2006/0041293 A1 * | 2/2006 | Mehdizadeh et al. | ........ 607/116 |
| 2007/0150007 A1 | 6/2007 | Anderson et al. | |
| 2007/0150036 A1 | 6/2007 | Anderson | |
| 2007/0155250 A1 * | 7/2007 | Mehdizadeh et al. | ........ 439/669 |
| 2007/0161294 A1 | 7/2007 | Brase et al. | |
| 2007/0219595 A1 | 9/2007 | He | |
| 2007/0239243 A1 | 10/2007 | Moffitt et al. | |
| 2008/0071320 A1 | 3/2008 | Brase | |
| 2008/0140168 A1 | 6/2008 | Walter et al. | |

OTHER PUBLICATIONS

U.S. Appl. No. 11/238,240, filed Sep. 29, 2005.
U.S. Appl. No. 11/694,769, filed Mar. 30, 2007.
U.S. Appl. No. 11/773,867, filed Jul. 5, 2007.
U.S. Appl. No. 11/855,033, filed Sep. 13, 2007.

* cited by examiner

*Primary Examiner* — Christopher D Koharski
*Assistant Examiner* — Roland Dinga
(74) *Attorney, Agent, or Firm* — Frommer Lawrence & Haug LLP; Bruce E. Black

(57) ABSTRACT

A lead has a first lead section; a second lead section; and a transition member disposed between the first and second lead sections at a transition site. Material of at least one of the first lead section and the second lead section passes through openings in the transition member.

17 Claims, 5 Drawing Sheets

LEAD WITH TRANSITION AND METHODS OF MANUFACTURE AND USE

FIELD

The present patent application is directed to leads for electrical stimulation systems, as well as the electrostimulation systems, and methods of manufacture and use of the leads and system. The present patent application is also directed to leads with a transition from one portion to another as well as electrical stimulation systems that include the leads, and methods of manufacture and use of the leads and system.

BACKGROUND

Implantable stimulation systems have been developed to provide therapy for a variety of disorders, as well as for other treatments. For example, stimulation systems can be used in neurological therapy by stimulating nerves or muscles, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

As one example, spinal cord stimulation is a well accepted clinical method for reducing pain in certain populations of patients. Stimulation systems have been developed to provide therapy for a variety of treatments. For example, stimulation systems can be used to stimulate nerves, such as the spinal cord, muscles, or other tissue. A stimulation system can include a control module (with a pulse generator) and one or more leads. Each lead can include an array of electrodes near a distal end of the lead and an array of control module contacts near a proximal end of the lead. The electrodes are in contact with or near the nerves, muscles, or other tissue to be stimulated. The control module contacts are in contact with corresponding contacts in the control module. The pulse generator in the control module generates electrical pulses that are transmitted through the control module/lead contacts, the lead, and the electrode for delivery to body tissue. As an example, electrical pulses can be provided to the dorsal column fibers within the spinal cord to provide spinal cord stimulation.

BRIEF SUMMARY

In one embodiment, a lead includes a first lead section; a second lead section; and a transition member disposed between the first and second lead sections at a transition site. Material of at least one of the first lead section and the second lead section passes through openings in the transition member.

In another embodiment, a lead includes a first lead section having at least one rib extending along a primary surface at a first end portion of the first lead section; and a second lead section. The second lead section and the first end portion of the first lead section overlap so that the rib(s) interacts with material of the second lead section to facilitate joining of the first and second lead sections.

In a third embodiment, a lead includes a first lead section and a second lead section. At least one of the first lead section or the second lead section comprises a stepped region disposed at an end of that lead section. The lead also includes a transition member disposed over the stepped region and coupling the first and second lead sections together at a transition site.

A stimulation system can include any of the leads described herein and an implantable control unit coupleable to the lead.

A method of making a lead includes joining a first lead portion and a second lead portion at a transition site; and disposing a transition member between the first and second lead portions with material of at least one of the first lead section and the second lead section passing through openings in the transition member to facilitate joining of the first and second lead portions.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present patent application is directed to leads for electrical stimulation systems, as well as the electrostimulation systems, and methods of manufacture and use of the leads and system. The present patent application is also directed to leads with a transition from one portion to another as well as electrical stimulation systems that include the leads, and methods of manufacture and use of the leads and system.

Suitable implantable electrical stimulation systems include, but are not limited to, an electrode lead with one or more electrodes disposed on a distal end of the lead and one or more terminals disposed on a proximal end of the lead. Electrodes leads include, for example, percutaneous leads, paddle leads, and cuff leads. Examples of electrical stimulation systems with electrode leads are found in, for example, U.S. Pat. Nos. 6,181,969; 6,516,227; 6,609,029; 6,609,032; and 6,741,892; and U.S. patent application Ser. Nos. 11/238,240; 11/319,291; 11/327,880; 11/375,638; 11/393,991; 11/396,309; 11/532,844; 11/609,586; 11/694,769; 11/773,867; and 11/855,033, all of which are incorporated by reference.

Figure 1:
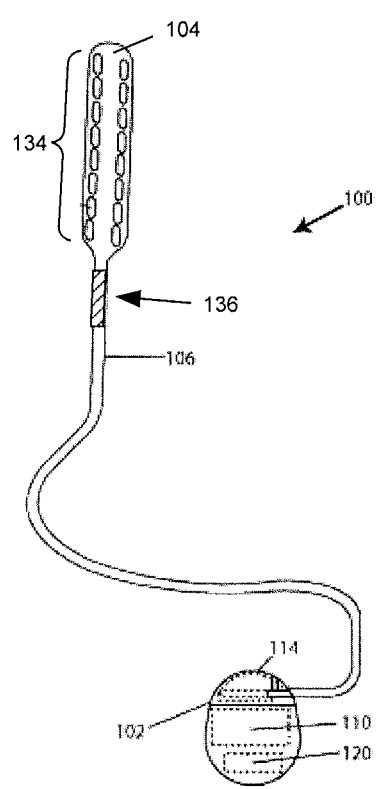
FIG. 1 is a schematic top view of one embodiment of a paddle lead, according to the invention.
Figure 2:
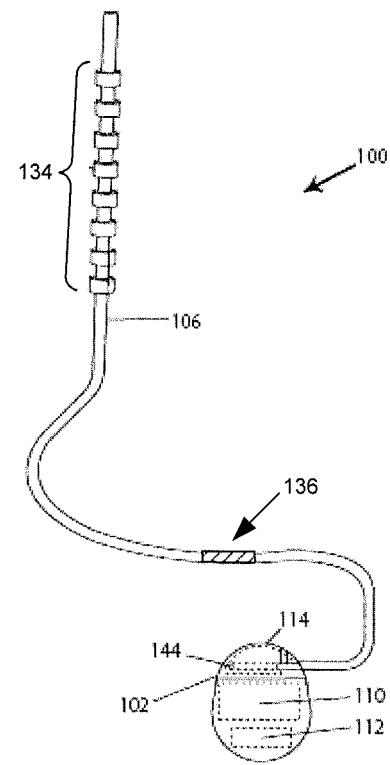
FIG. 2 is a schematic top view of one embodiment of a percutaneous lead, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the lead body 106 form a lead. The paddle body 104 typically includes an array of electrodes 134. The control module 102 typically includes an electronic subassembly 110 and optional power source 120 disposed in a sealed housing 114. The control module 102 typically includes a connector 144 (see FIG. 2) into which the proximal end of the lead body 106 can be plugged to make an electrical connection via conductive contacts on the control module 102 and on the lead body 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions (not shown) can be disposed between the lead and the control module 102 to extend the distance between the control module 102 and the lead body 106 of the embodiments shown in FIGS. 1 and 2.

The electrical stimulation system or components of the electrical stimulation system, including one or more of the lead body 106, the paddle body 104 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or lead body 106, as well conductive contacts on the proximal end of the lead, are typically disposed in, or separated by, a non-conductive, biocompatible material including, for example, silicone, polyurethane, polyetheretherketone ("PEEK"), epoxy, and the like or combinations thereof. The paddle body 104 and lead body 106 may be formed in the desired shape by any process including, for example, molding (including injection molding), casting, and the like. The non-conductive material typically extends from the distal end of the lead to the proximal end. The non-conductive, biocompatible material of the paddle body 104 and the lead body 106 may be the same or different. The paddle body 104 and lead body 106 may be a unitary structure or can be formed as two separate structures that are permanently or detachably coupled together.

Conductive contacts (not shown) are typically disposed at the proximal end of the lead for connection to a corresponding conductive contact (not shown in FIG. 1) in the control module 102 (or to conductive contacts on a lead extension). Conductor wires extend from the conductive contacts to the electrodes 134. Typically, one or more electrodes 134 are electrically connected to a conductive contact. In some embodiments, each conductive contact is only connected to one electrode 134. The conductor wires may be embedded in the non-conductive material of the lead or can be disposed in one or more lumens 150 (see FIG. 6) extending along the lead. In some embodiments, there is an individual lumen for each conductor wire. In other embodiments, two or more conductor wires may extend through a lumen. There may also be one or more lumens that open at, or near, the proximal end of the lead, for example, for inserting a stylet rod to facilitate placement of the lead within the body of a patient. Additionally, there may also be one or more lumens that open at, or near, the distal end of the lead, for example, for infusion of drugs or medication into the site of implantation of the paddle body 104.

Leads can be formed using a variety of materials. The choice of materials for lead construction can depend on a variety of factors including, for example, ease of manufacture, cost, production time, biocompatibility, mechanical properties (e.g., flexibility, tensile strength, tear strength, and elongation), biostability, handling properties, and the like. Leads can be produced using different materials along different parts of the lead. For example, a distal end (e.g., a paddle body 104 and, optionally, a portion of the lead 106 near the paddle body or a portion of the lead of FIG. 2 proximate to the electrodes 134) can be made of one material, for example, silicone or polyurethane, and the proximal end of the lead 106 can be made using another material, for example, polyurethane or PEEK. As one example, silicone may be selected for the distal end of the lead 106 because it is easier to form the electrode array 134 using the silicone material for a paddle body 104 or other portion of the lead 106 near the electrodes. Polyurethane may be selected for the proximal end because it has better properties for the formation of a connector with an implantable pulse generator or lead extension. In these leads, the two portions of the lead made of different materials couple together at a transition site 136. The transition site can generally be any suitable site along the length of the lead 106 between the proximal and distal ends. Transition sites can also occur even when the two portions of the lead are made of the same material and later joined together. FIG. 1 illustrates a transition site 136 near a paddle body 104 and FIG. 2 illustrates a transition site near a center of a lead. It will be recognized, however, that the transition site can be positioned at other points along the lead and that a lead may contain more than one transition site.

Conventionally, a sleeve over the transition site has been used to couple the two portions of the lead together. A sleeve, however, will typically increase the diameter of the lead at the transition site which may be undesirable, particularly for percutaneous delivery of the lead because a larger diameter introducer may be needed to accommodate the larger diameter of the lead at the transition site.

Figure 3:
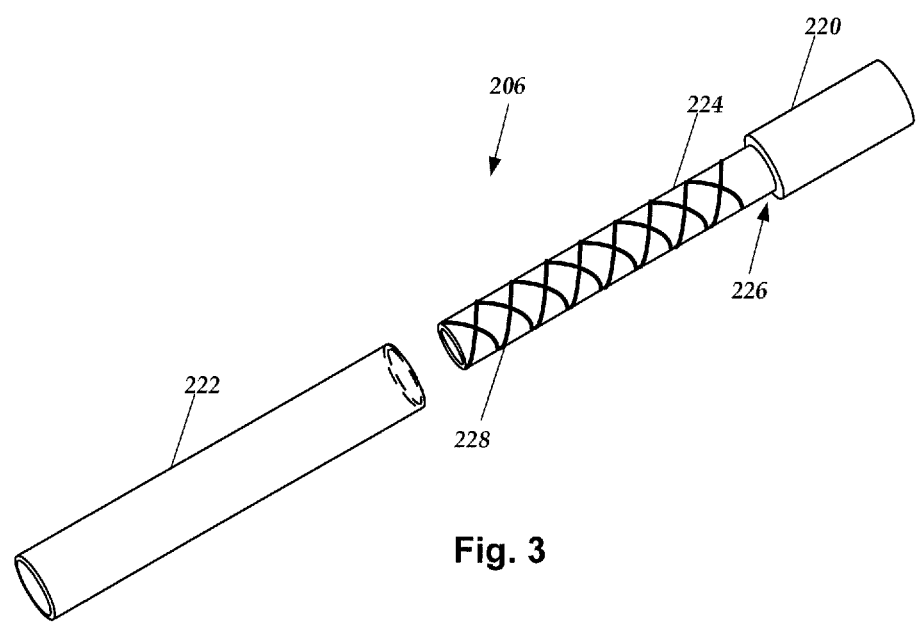
FIG. 3 is a schematic perspective view of one embodiment of a transition site of a lead containing a transition element to facilitate the coupling the two portions of the lead, according to the invention.

Instead of a sleeve, the two portions of the lead at the transition site can be coupled by modifying the ends of the portions to form a connecting arrangement. FIG. 3 illustrates one embodiment of a transition site of a lead 206. The lead includes a first lead portion 220 made of a first material and a second lead portion 222 made of second material. For example, the first material can be silicone and the second material can be a polyurethane, or vice versa. It will be recognized that the first lead portion can be either the distal or proximal portion of the lead and that the second lead portion is then the proximal or distal portion of the lead, respectively.

The first lead portion 220 has a smaller diameter region 224 at an end of the lead portion 220. This smaller diameter region 224 can be a stepped region (with one of more steps 226) as illustrated in FIG. 3, or can be tapered so that the outer diameter of the region 224 becomes progressively smaller, or any combination of stepped and tapered arrangements. The smaller diameter region 224 of the first lead portion 220 can then be received within an end of the second lead portion 222 of the lead.

In one embodiment, a transition member 228 is provided between the smaller diameter region 224 of the first lead portion 220 and the second lead portion 222. The transition member 228 can be any suitable element that facilitates coupling between the first and second lead portions and preferably strengthens the joint between the first and second lead portions. For example, the transition member can be a weave, a web, a helix, a spiral, or any other arrangement that provides openings between portions of the transition member through which the material of one, or both of, the first and second lead portions can pass.

The transition member can be made of a different material than the first and second lead portions. For example, the transition member can be made of, for example, a thermoplastic or metal material. Suitable materials can include, for example, nylon, polyester, polyetheretherketone (PEEK), polysulfone, polycarbonate, acrylonitrile butadiene styrene polymers, stainless steel, nitonol, titanium, platinum, platinum/iridium, and the like. The transition member is incorporated into the transition site to facilitate binding of the transition site or to strengthen the joint at the transition site or both.

The material of the first lead portion 220, the second lead portion 222, or both can be molded around the transition member 228 at the transition site to create mechanical interlocks through the openings in the transition member. For example, the first lead portion 220 or second lead portion 222 or both can be heated at the transition site to mold the material(s) of the portion(s) around the transition member 228. As another example, the first lead portion 220 or second lead portion 222 or both can be heated at the transition site to reflow the material(s) of the portion(s) around the transition member 228. As yet another example, the second lead portion 222 can be overmolded on and around the transition member 228 disposed on the first lead portion 220. Alternatively, the two portions can be joined using an interference fit or any combinations of the joining methods described herein.

Figure 4:
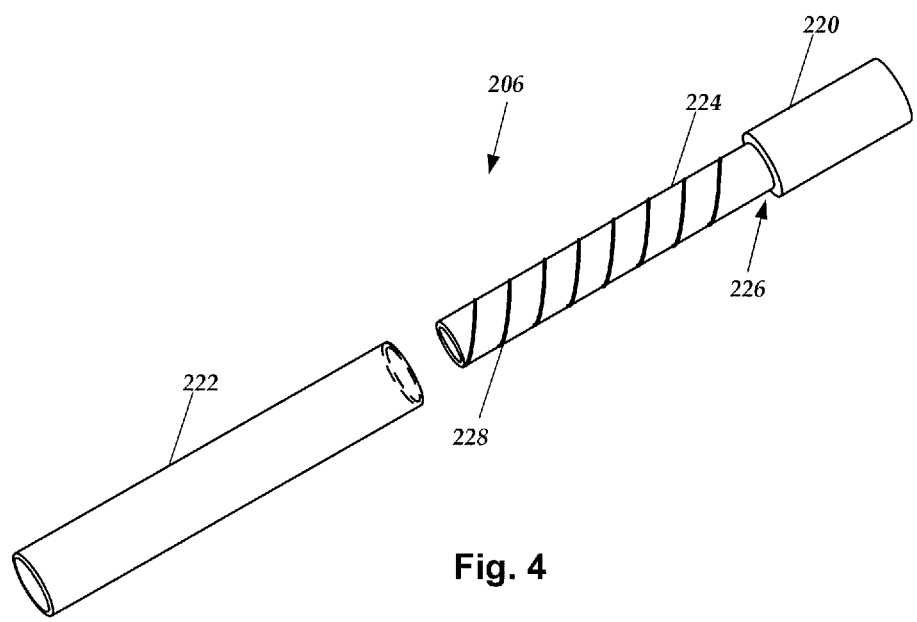
FIG. 4 is a schematic perspective view of another embodiment of a transition site of a lead containing a transition element to facilitate the coupling the two portions of the lead, according to the invention.
Figures 5, 6:
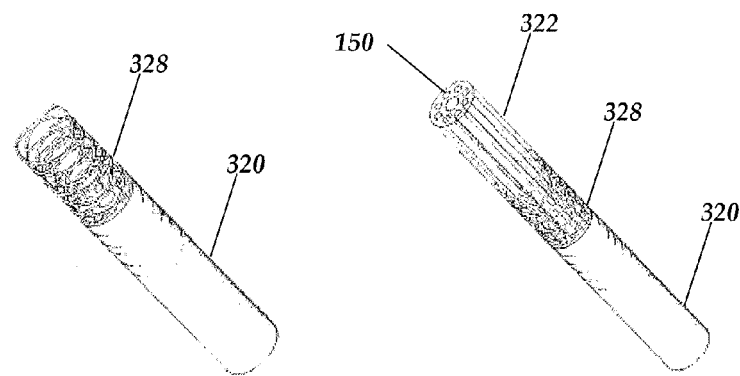
FIG. 5 is a schematic perspective view of a portion of a third embodiment of a transition site of a lead containing a transition element to facilitate the coupling the two portions of the lead, according to the invention.
FIG. 6 is a schematic perspective view of the transition site of FIG. 5 with both portions of the lead represented, according to the invention.

FIG. 3 illustrates a transition member 228 in the form of a weave. FIG. 4 illustrates a transition member 228 in the form of a spiral or helix. FIGS. 5 and 6 illustrate yet another embodiment in which the transition member 228 is in the form of a spiral or helix where one or both of the first and second lead portions is molded, for example, injection molded, around the transition member 228. The transition member 228 can be initially disposed on the first lead portion 220 or can be incorporated into the material (e.g., through overmolding, reflowing, or any other suitable method) of the first or second lead portions prior to joining the two lead portions. The transition member 228 may extend over the length of the transition site, beyond the transition site, or over only a portion of the transition site. The pitch of a weave, web, spiral, or helix can be uniform or can vary.

FIGS. 5 and 6 also illustrate another embodiment in which the first lead portion 320 is not necessarily inserted into the second lead portion 322. Instead, the two lead portions 320, 322 are coupled together by a transition member 328 that extends between the two portions. For example, the two portions 320, 322 can be overmolded or reflowed over the transition member 328. This arrangement can be used to form a transition isodiametric with adjacent portions of the lead 306 if desired.

Figure 7:
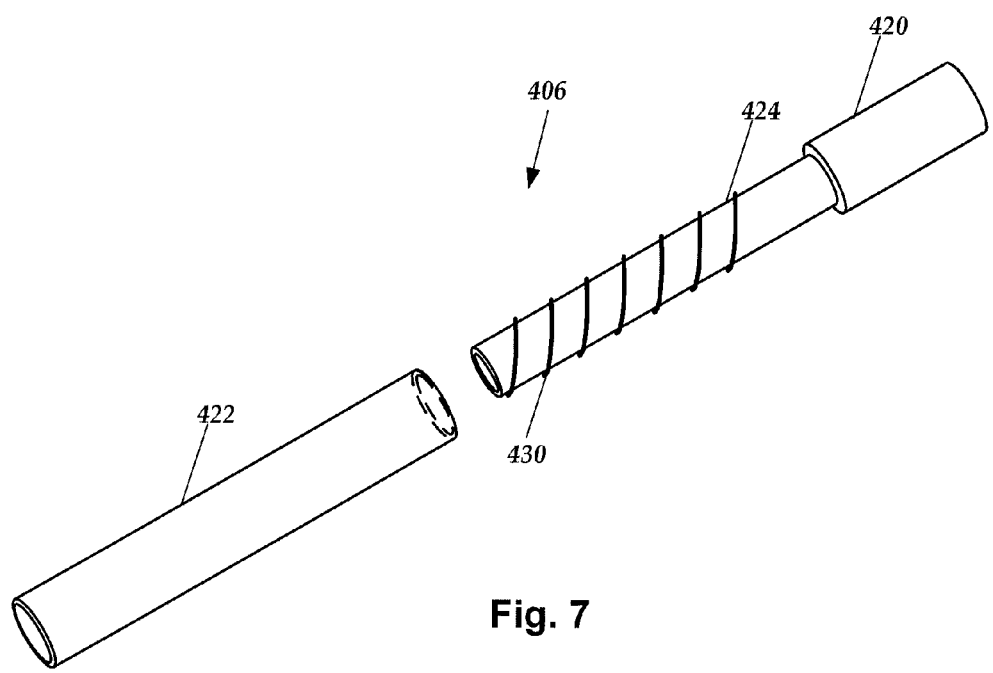
FIG. 7 is a schematic perspective view of a portion of an embodiment of a transition site of a lead containing ribs to facilitate the coupling the two portions of the lead, according to the invention.

In another embodiment, a lead 406 has a first lead portion 420 with one or more ribs 430 along at least a portion of the smaller diameter region 424 as illustrated, for example, in FIG. 7. The ribs extend beyond the remainder of the surface of the first lead portion 420 and interact with the second lead portion (not shown) of the lead when the smaller diameter region 424 is inserted. It will be recognized that, alternatively or additionally, ribs can extend from the inner surface of a region at or near the end the second lead portion 422 to interact with the first lead portion 420 of the lead when it is inserted. The rib(s) can be formed in any pattern including, but not limited to, a spiral, a helix, a double helix, knurl, ring(s), or the like. The pitch of the ribs can be uniform or can vary. The transition member 428 may extend over the length of the transition site, beyond the transition site, or over only a portion of the transition site.

A transition member, as discussed above with respect to the preceding embodiments, can be used in conjunction with ribs on the first lead portion, second lead portion, or both. In addition to, and in conjunction with, a transition member, ribs, or both as discussed above, other mechanisms for joining the lead portions optionally can be used including, for example, adhesive, a sleeve over at least a portion of the joint, and the like.

Figure 8A:
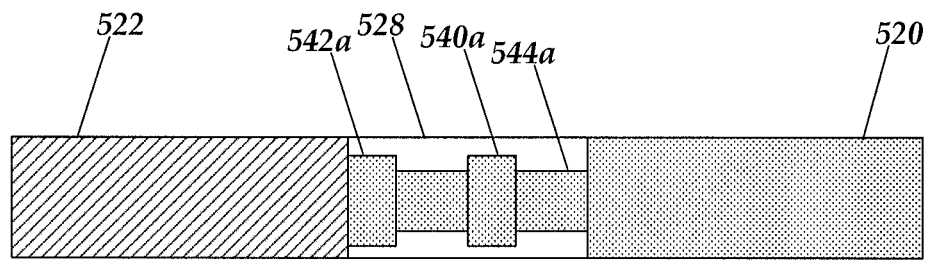
FIG. 8A is a schematic longitudinal cross-sectional perspective view of a fourth embodiment of a transition site of a lead, according to the invention.
Figure 8B:
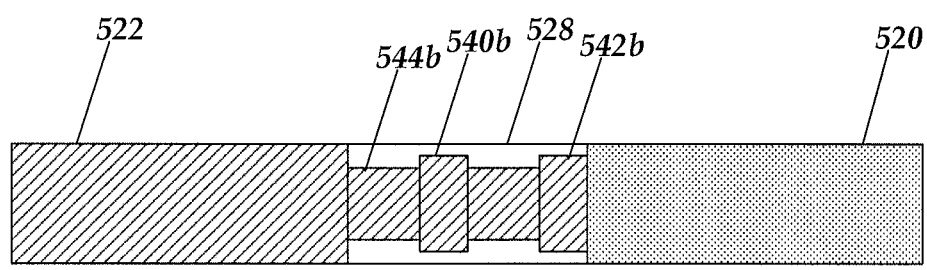
FIG. 8B is a schematic longitudinal cross-sectional perspective view of a fifth embodiment of a transition site of a lead, according to the invention.
Figure 8C:
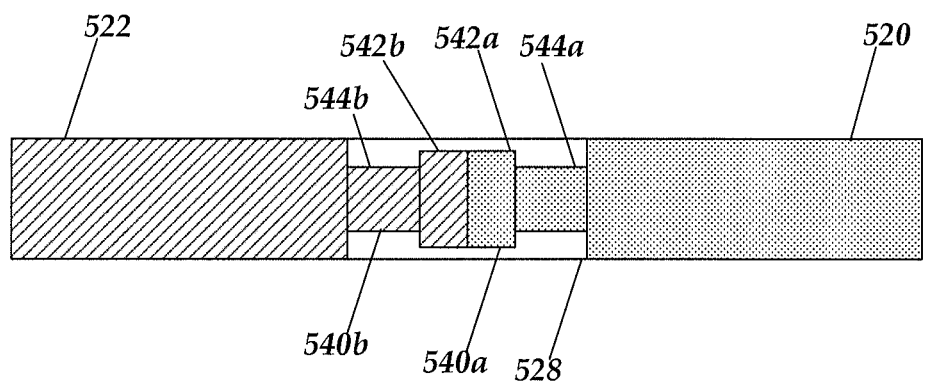
FIG. 8C is a schematic longitudinal cross-sectional perspective view of a sixth embodiment of a transition site of a lead, according to the invention.

FIGS. 8A, 8B, and 8C illustrate yet another embodiment in which one, or both, of the lead portions 520, 522 includes a stepped region 540a, 540b over which a transition member 528 is overmolded to form a transition isodiametric with adjacent portions of the lead. The stepped region 540a, 540b may include one or more steps and when the region includes multiple steps the steps may be the same size or different sizes. In some instances, as illustrated in FIGS. 8A, 8B, and 8C, the stepped region may include portions 542a, 542b that are larger in diameter than other portions 544a, 544b and the smaller diameter portions may be disposed between the larger diameter portions and the remainder of the lead. FIG. 8A illustrates an embodiment in which lead portion 520 has a stepped region 540a. FIG. 8B illustrates an embodiment in which lead portion 522 has a stepped region 540b. FIG. 8C illustrates an embodiment in which both lead portions 520, 522 have respective stepped regions 540a, 540b.

The transition member 528 can be made of the same material as lead portion 520 or lead portion 522 or the transition member can be made of an entirely different material or a combination of the materials of lead portions 520, 522. Preferably, the material of the transition member 528 bonds or adheres to the material(s) of the lead portions 520, 522. The transition member 528 can simply be material overmolded over the stepped region(s) 540a, 540b or the transition member 528 may also include a structured element such as a weave, a web, a helix, or a spiral within the material the forms the transition member 528.

Figure 9:
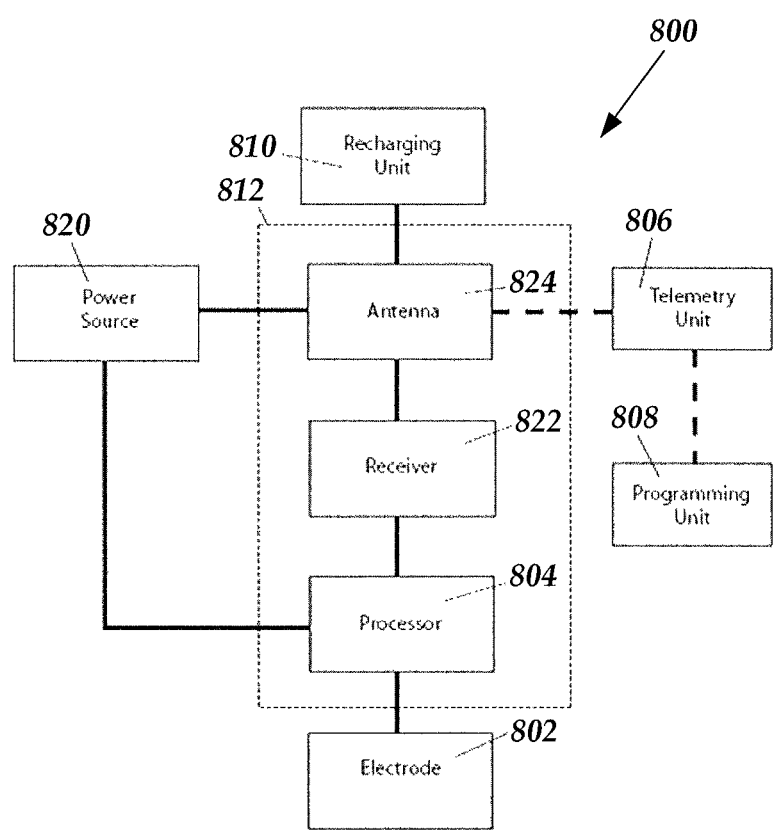
FIG. 9 is a schematic overview of one embodiment of components of a stimulation system, including an electronic subassembly disposed within a control module, according to the invention.

FIG. 9 is a schematic overview of one embodiment of components of a stimulation system 800 including an electronic subassembly 812 disposed within a control module and coupled to one or more electrodes 802 via a lead. It will be understood that the stimulation system can include more, fewer, or different components and can have a variety of different configurations including those configurations disclosed in the stimulator references cited herein.

Some of the components (for example, power source 820, antenna 824, receiver 822, and processor 804) of the stimulation system can be positioned on one or more circuit boards or similar carriers within a housing of an implantable pulse generator, if desired. Any power source 820 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 824 or a secondary antenna. The external power source can be in a device that is mounted on the skin of the user or in a unit that is provided near the user on a permanent or periodic basis.

If the power source 820 is a rechargeable battery, the battery may be recharged using the optional antenna 824, if desired. Power can be provided to the battery for recharging by inductively coupling the battery through the antenna to a recharging unit 216 external to the user. Examples of such arrangements can be found in the references identified above.

In one embodiment, electrical current is emitted by the electrodes 802 on the paddle or lead body to stimulate nerve fibers, muscle fibers, or other body tissues near the stimulation system. A processor 804 is generally included to control the timing and electrical characteristics of the stimulation system. For example, the processor can, if desired, control one or more of the timing, frequency, strength, duration, and waveform of the pulses. In addition, the processor 804 can select which electrodes can be used to provide stimulation, if desired. In some embodiments, the processor may select which electrode(s) are cathodes and which electrode(s) are anodes. In some embodiments, the processor may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allow modification of pulse characteristics. In the illustrated embodiment, the processor 804 is coupled to a receiver 822 which, in turn, is coupled to the optional antenna 824. This allows the processor to receive instructions from an external source to, for example, direct the pulse characteristics and the selection of electrodes, if desired.

In one embodiment, the antenna 824 is capable of receiving signals (e.g., RF signals) from an external telemetry unit 806 which is programmed by a programming unit 808. The programming unit 808 can be external to, or part of, the telemetry unit 806. The telemetry unit 806 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 808 can be any unit that can provide information to the telemetry unit for transmission to the stimulation system. The programming unit 808 can be part of the telemetry unit 806 or can provide signals or information to the telemetry unit via a wireless or wired connection. One example of a suitable programming unit is a computer operated by the user or clinician to send signals to the telemetry unit.

The signals sent to the processor 804 via the antenna 824 and receiver 822 can be used to modify or otherwise direct the operation of the stimulation system. For example, the signals may be used to modify the pulses of the stimulation system such as modifying one or more of pulse duration, pulse frequency, pulse waveform, and pulse strength. The signals may also direct the stimulation system to cease operation or to start operation or to start charging the battery. In other embodiments, the stimulation system does not include an antenna 824 or receiver 822 and the processor 804 operates as programmed.

Optionally, the stimulation system may include a transmitter (not shown) coupled to the processor and antenna for transmitting signals back to the telemetry unit 806 or another unit capable of receiving the signals. For example, the stimulation system may transmit signals indicating whether the stimulation system is operating properly or not or indicating when the battery needs to be charged. The processor may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected is:

1. A lead, comprising:
   a first lead section having a proximal end and a distal end;
   a plurality of conductive contacts disposed along the proximal end of the first lead section;
   a second lead section having a proximal end and a distal end;
   a plurality of electrodes disposed along the distal end of the second lead section; and
   a transition member disposed radially between the distal end of the first lead section and the proximal end of the second lead section at a transition site, wherein the transition member comprises a first opening in a first end, a second opening in a second end, and a plurality of additional openings between the first and second ends of the transition member, wherein material of at least one of the first lead section and the second lead section passes through the additional openings in the transition member to facilitate joining the first lead section to the second lead section.

2. The lead of claim 1, wherein the first lead section comprises a first material and the second lead section comprises a second material different from the first material.

3. The lead of claim 2, wherein the first material is polyurethane and the second material is silicone.

4. The lead of claim 2, wherein the first material is silicone and the second material is polyurethane.

5. The lead of claim 1, wherein the lead is isodiametric along the transition site and portions of the first and second lead sections adjacent the transition member.

6. The lead of claim 1, wherein the distal end of the first lead section has an outer diameter smaller than a portion of the first lead section adjacent the distal end and wherein the transition member is at least partially disposed over the distal end of the first lead section.

7. The lead of claim 6, wherein the distal end of the first lead section is stepped.

8. The lead of claim 6, wherein the transition member is a weave with a helical, spiral, or double helical shape disposed on the distal end of the first lead section with the smaller outer diameter.

9. The lead of claim 1, wherein the transition member is a weave with a helical, spiral, or double helical shape.

10. The lead of claim 1, wherein the first lead section comprises at least one rib extending along a primary surface of the distal end of the first lead section, wherein the second lead section and the distal end of the first lead section overlap so that the at least one rib interacts with material of the second lead section to facilitate joining of the first and second lead sections.

11. The lead of claim 1, wherein the second lead section comprises at least one rib extending along a primary surface of the proximal end of the second lead section, wherein the first lead section and the proximal end of the second lead section overlap so that the at least one rib interacts with material of the first lead section to facilitate joining of the first and second lead sections.

12. The lead of claim 1, wherein the distal end of the first lead section comprises a first portion that has an outer diameter smaller than a portion of the first lead section proximally adjacent the distal end and a second portion, distal to the first portion, that has an outer diameter larger then the first portion, wherein the transition member is at least partially disposed over the first and second portions of the distal end of the first lead section.

13. The lead of claim 1, wherein the proximal end of the second lead section comprises a first portion that has an outer diameter smaller than a portion of the second lead section distally adjacent the proximal end and a second port on, proximal to the first portion, that has an outer diameter larger then the first portion, wherein the transition member is at least partially disposed over the first and second portions of the proximal end of the second lead section.

14. A method of making a lead, the method comprising
joining a first lead portion and a second lead portion at a transition site, wherein the lead comprises a plurality of conductive contacts disposed along a proximal end of the first lead portion and a plurality of electrodes disposed along a distal end of the second lead portion; and
disposing a transition member radially between the distal end of the first lead portion and the proximal end of the second lead portion, wherein the transition member comprises a first opening in a first end, a second opening in a second end, and a plurality of additional openings between the first and second ends of the transition member with material of at least one of the first lead portion and the second lead portion passing through the additional openings in the transition member to facilitate joining of the first and second lead portions.

15. The method of claim 14, wherein disposing a transition member comprises, prior to joining the first and second lead portions, disposing the transition member on the distal end of the first lead portion that has an outer diameter smaller than a portion of the first lead portion adjacent the distal end.

16. The method of claim 15, wherein disposing the transition member on the distal end of the first lead portion comprising disposing the transition member on the distal end of the first lead portion, wherein the distal end is tapered.

17. The method of claim 15, wherein disposing the transition member on the distal end of the first lead portion comprising disposing the transition member on the distal end of the first lead portion, wherein the distal end is stepped.

* * * * *